United States Patent [19]

Peterson et al.

[11] 4,448,062
[45] May 15, 1984

[54] METHOD AND APPARATUS FOR EROSION DETECTION AND LOCATION IN HYDROCARBON PRODUCTION SYSTEMS AND THE LIKE

[75] Inventors: Marvin L. Peterson; Norman W. Hein, Jr., both of Ponca City, Okla.

[73] Assignee: Conoco Inc., Ponca City, Okla.

[21] Appl. No.: 313,902

[22] Filed: Oct. 22, 1981

[51] Int. Cl.³ ............................................. G01N 29/00
[52] U.S. Cl. ......................................... 73/86; 73/587; 73/658
[58] Field of Search .................... 73/587, 801, 86, 658, 73/659

[56] References Cited

U.S. PATENT DOCUMENTS

| | | |
|---|---|---|
| 3,228,232 | 1/1966 | Proctor . |
| 3,384,181 | 5/1968 | Maly et al. . |
| 3,509,764 | 5/1970 | Baldwin et al. . |
| 3,563,311 | 2/1971 | Stein . |
| 3,816,773 | 6/1974 | Baldwin et al. . |
| 3,841,144 | 10/1974 | Baldwin . |
| 3,854,323 | 12/1974 | Hearn et al. . |
| 3,906,780 | 9/1975 | Baldwin et al. . |
| 3,908,454 | 9/1975 | Mullins et al. . |
| 4,015,464 | 4/1977 | Miller et al. . |
| 4,033,179 | 7/1977 | Romrell .............................. 73/587 |
| 4,112,773 | 9/1978 | Abts . |
| 4,297,885 | 11/1981 | Hein, Sr. et al. ..................... 73/587 |

FOREIGN PATENT DOCUMENTS

| | | | |
|---|---|---|---|
| 49401 | 4/1982 | European Pat. Off. ............... | 73/587 |
| 52-14476 | 2/1977 | Japan ..................................... | 73/587 |
| 54-48292 | 4/1979 | Japan ..................................... | 73/587 |

OTHER PUBLICATIONS

The Use of Acoustic Emission to Detect Incipient Failure in Pressure Vessels; by R. Bell; Kerntechnik, vol. 16, No. 5, pp. 216–222, May 1974.
Mullins, Baldwin and Berry, Surface Flowline Sand Detection, Society of Petroleum Engineers (SPE) Paper No. 5152, (1974).
Foster and Linville, A Method of Monitoring and Production In a Flowing Well Stream, SPE Paper No. 8214, (1979).
Material from Oceanography International Corporation entitled Sonic Sand Detector, (1974), An Evaluation Report—The Sonic Sand Detector, (1974), and Flowline Sand Detector/Monitor, (1978).
Stuivenwold and Mast, New Instrumentation for Managing Sand-Problem Prone Fields SPE, Paper No. 9368, (1980).
Swan and Reiner, Sand Probes Trim Equipment Erosion, Oil and Gas J. 45, (May 27, 1974).

*Primary Examiner*—Stephen A. Kreitman
*Attorney, Agent, or Firm*—A. Joe Reinert

[57] ABSTRACT

Acoustic emissions are detected so that the amount of wear on the interior of a conduit can be directly determined. The acoustic emissions arise from plastic deformations and fractures caused by the fluid and particulate substances therein flowing through the conduit and impinging upon the interior surface of the conduit or by cavitation. The apparatus as disclosed has the capability to detect and also locate the surface area where wear is occurring.

8 Claims, 2 Drawing Figures

METHOD AND APPARATUS FOR EROSION DETECTION AND LOCATION IN HYDROCARBON PRODUCTION SYSTEMS AND THE LIKE

BACKGROUND OF THE INVENTION

This invention relates generally to methods and apparatus for detecting and locating wear of a conduit carrying a flowing substance and more particularly, but not by way of limitation, to methods and apparatus for detecting and locating the loss of metal from the interior surfaces of production equipment and flow lines used for transporting hydrocarbons and entrained particulate substances in a hydrocarbon production system.

Substances flowing through conduits (conduits being defined to include fluid-carrying elements such as may be found, for example, in hydrocarbon production equipment including valves, pumps, tubing, processing equipment, pipelines and the like) tend to wear the interior surfaces of the conduits. In particular, erosion occurs in an oil production conduit through which hydrocarbons having sand and other particulate substances entrained therein flow from a well. Erosion of the conduit occurs when the entrained particles impact on the interior surface of the conduit. Erosion can also be caused by cavitation which is the process where pressure differences cause bubbles to form in the flowing substance and to collapse at the interface between the flowing substance and a pipeline, for example, thereby producing wear on the pipeline. Erosion especially occurs within the pipeline on the outside of a turn just downstream of a change in direction of the flow or where there is a large change in pressure.

It is important to detect this erosion because if the erosion is allowed to continue, the conduit can fail when the wall thickness is reduced to the extent that the wall thickness can no longer withstand the pressure exerted by the flowing substance. Conduit failure can adversely affect the environment and the hydrocarbon production system. More generally, these wear processes can similarly affect an overall hydrocarbon production system and the production equipment contained therein.

Several types of devices contemplated to be used to determine the particulate content of a flowing fluid have been proposed. By monitoring the particulate (e.g., sand) content of the flow, these devices are proposed to be able to determine the amount of erosion caused by particulate impingement. Such devices have proposed the use of flow sampling and filtering techniques and the utilization of erodable sensors. However, very few devices can detect cavitation erosion.

One of the devices for monitoring erosion is disclosed in U.S. Pat. No. 3,906,780 to Baldwin. This patent discloses a means for continuously monitoring a fluid stream in a conduit to indicate the presence or increased presence of particulate material, such as sand, in the fluid stream. The continouos monitoring is disclosed to occur by detecting in the conduit vibrations, or "pinges," caused by the kinetic energy given up by the fluid stream as it impinges on the inner surface of the conduit and by generating electrical signals having frequencies representative of the vibrations and, thus, the kinetic energy. The Baldwin patent discloses that these vibrations have frequencies in excess of 100 kilohertz. It appears from the Baldwin patent that higher frequencies of the order of 700 kilohertz are preferable to detect because the Baldwin patent mentions that background noise up to 250 kilohertz has been detected without indicating the kinetic energy given up by the sand impinging upon the interior of the conduit. In other printed documents pertaining to a sand detector device related to the device described in the Baldwin patent, it is stated that the desirable frequencies to monitor are within the range between 650 kilohertz and 750 kilohertz. See, Mullins, Baldwin and Berry, *Surface Flowline Sand Detection*, Society of Petroleum Engineers (SPE) Paper No. 5152 (1974); Foster and Linville, *A Method of Monitoring Sand Production in a Flowing Well Stream*, SPE Paper No. 8214 (1979); and material from Oceanography International Corporation pertaining to the Sonic Sand Detector [entitled *Sonic Sand Detector* (1974), *An Evaluation Report—The Sonic Sand Detector* (1974), and *Flowline Sand Detector/Monitor* (1978)]. Related disclosures are set forth in U.S. Pat. No. 3,816,773 to Baldwin et al. and U.S. Pat. No. 3,841,144 to Baldwin.

Other types of apparatus and methods are disclosed in U.S. Pat. No. 3,384,181 to Maly et al., U.S. Pat. No. 3,854,323 to Hearn et al., U.S. Pat. No. 3,908,454 to Mullins, in Stuivenwold and Mast, *New Instrumentation for Managing Sand-Problem Prone Fields*, SPE Paper No. 9368 (1980), and in Swan and Reimer, *Sand Probes Trim Equipment Erosion*, Oil & Gas J. 45 (May 27, 1974). Sound responsive devices and methods proposed to be used in investigating blast effects are disclosed in U.S. Pat. No. 3,509,764 to Baldwin et al. and U.S. Pat. No. 3,563,311 to Stein.

In addition to merely detecting that wear is occurring in a conduit, it is important to locate where in the conduit the wear is occurring. This is important because, for example, if the wear is occurring at a specific location, failure may occur relatively quickly, whereas if the wear is only occurring continuously along the length of the conduit, then failure may not occur as quickly.

Although various methods and devcies have been proposed, such methods and devices have several shortcomings. For example, these devices generally lack the desirable sensitivity by which the erosion can be accurately determined. They also cannot locate precisely the area where wear is occurring. Additionally, there is generally no means for providing instantaneous readings of the erosion damage. Furthermore, several of the proposed systems require that equipment be inserted into the flow stream. This requires shutting down production while the equipment is installed or modified. The insertion of equipment into the flow stream also increases the turbulence which increases the erosion thereby further shortening the life of the conduit. Additionally, the inserted equipment, such as probes, are generally eventually destroyed by erosion; thus the life of the inserted probe is limited. These devices also generally have the shortcoming of being difficult to calibrate because they detect the sand content of the flow stream rather than the actual metal loss of the conduit. Because metal loss does not always occur merely because there is sand present, it is difficult to accurately correlate the sand content to the actual erosion damage.

Therefore, there is the need for an apparatus and a method for determining a direct indication of the actual erosion, and the location thereof, resulting from a particulate substance impacting on or from a cavitation process acting on the interior of the conduit. Such apparatus and method should provide accurate, reliable and instantaneous detection of the actual extent of erosion. The apparatus should also be attachable to existing systems without having to shut down the systems.

SUMMARY OF THE INVENTION

The present invention overcomes the above-noted and other shortcomings of the prior art by providing a novel and improved method and apparatus for detecting and locating the deterioration by erosion of a conduit, such as may be found in hydrocarbon production equipment for example, carrying a flowing substance. The apparatus and method yield a direct indication of the actual erosion because the present invention can detect the phenomena directly associated with the actual erosion including the actual impingement of any entrained particles.

Broadly, the method of the present invention includes sensing acoustic emission energy generated by the interaction between a conduit and a substance flowing through the conduit. The method als includes determining the deterioration of the conduit based on the sensed acoustic emission energy.

The sensing of the acoustic emission energy includes detecting stress waves which are produced by the plastic deformation and/or fracturing of portions of the conduit. These phenomena occur in response to the interaction between the flowing substance and the conduit. The detected stress waves preferably include those having frequencies within the range of frequencies between approximately 100 kilohertz and approximately 500 kilohertz. However, higher or lower frequencies may be emitted during erosion.

The apparatus of the present invention includes transducer means for detecting the acoustic emissions, filter means for electrically passing those of certain electrical signals generated by the transducer means in response to the detected acoustic emissions and having frequencies within a predetermined range, microprocessor means for interpreting the erosion of the conduit based on the detected acoustic emissions, and communication means for communicating the acoustic emission information. If specific location determination capabilities are required, multiple transducers, filters, and preamplifiers would be necessary. However, single transducer, filter and preamplifier will be able to detect wear at a general location corresponding to or in the vicinity of its area of attachment.

Therefore, from the foregoing it is a general object of the present invention to provide a novel and improved method and apparatus for detecting and locating the deterioration of a conduit carrying a flowing substance. Other and further objects, features and advantages of the present invention will be readily apparent to those skilled in the art when the following description of the preferred embodiment is read in conjunction with the accompanying drawings.

DETAILED DESCRIPTION OF THE PREFERRED EMBODIMENT

Figure 1:
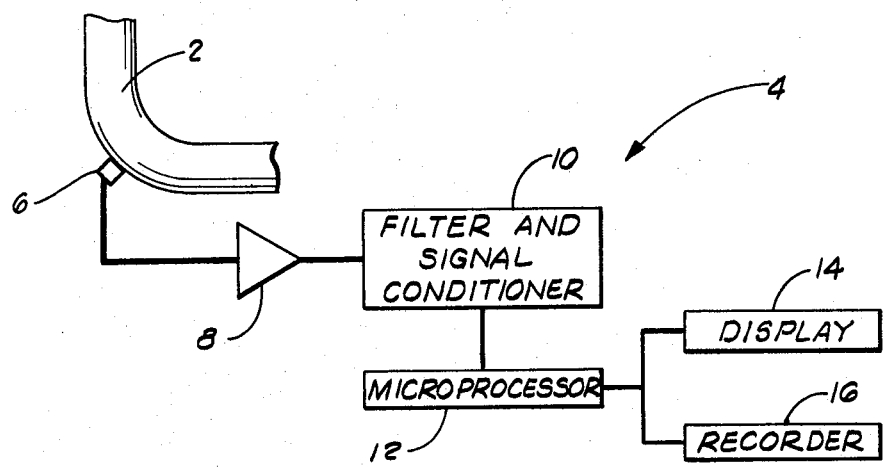
FIG. 1 is a functional block diagram schematically illustrating the preferred embodiment of the apparatus of the present invention.

With reference to the drawings the preferred embodiment of the present invention will be described. In FIG. 1 there is schematically disclosed a fluid-carrying conduit 2 through which hydrocarbons are flowed from a producing well. The conduit 2 can represent a fluid-carrying portion of production equipment such as a valve, pump, tubing, pipeline or the like, but the conduit 2 is not limited to such devices. The stream flowing through the conduit 2 interacts with the interior surface of the conduit 2 so that wear occurs. In the example of a production conduit pipeline having hydrocarbons flowing therethrough, the hydrocarbons often have a particulate substance (or substances), such as sand, entrained therein. The entrained substance causes or enhances the erosion of the inner surface of the conduit 2. The wear processes acting on the conduit cause structural conduit material, such as metal, to be lost as the flowing stream interacts with the conduit 2. The erosion can also occur by cavitation wherein bubbles or voids formed in the flowing hydrocarbons, such as by turbulence, collapse on the interior of the conduit 2 and thereby erode a portion of the conduit 2.

To detect the amount of wear of the interior surface of the conduit 2, the present invention includes the apparatus functionally shown in block format in FIG. 1 and labeled generally by the reference numeral 4. The apparatus 4 includes means for sensing the energy released when the material of the conduit 2 is plastically deformed and/or separated from the conduit as the fluid and entrained particulate substance, if any, flows through the conduit 2. The sensing means includes a transducer means 6 of a suitable type known in the art for detecting the energy released from the plastic deformation and/or separation processes.

For specific location of wear purposes, multiple transducer means 6 can be used. For example, if two transducer means 6 are attached to the conduit 2 at spaced locations, the specific location of the wear process can be determined by knowing the speed of transmission of the energy through the conduit 2 and by noting the time differential between when a first one of the transducer means detects the energy release and when a second one of the transducer means detects the energy release and by then computing the location. The computations needed to derive the location are known in the art.

The transducer means 6 detects the acoustic emission energy propagated through the conduit 2 when a plastic deformation or a fracture occurs in the conduit 2. Upon detecting this energy, the transducer means 6 converts it into corresponding time-varying electrical signals which have frequencies corresponding to the detected frequencies of the emitted energy. In the preferred embodiment the transducer means 6 is responsive to a predetermined first range of frequencies of the released energy. That is, although the released energy may have frequency components over a relatively wide spectrum, the transducer means preferably detects only a first range of frequencies of the wider spectrum. The preferred first range of frequencies includes the frequencies of approximately 100 kilohertz to approximately 500 kilohertz. This range is preferred because it has been found to be above the noise associated with the fluid flow of a hydrocarbon stream through a pipeline and to still allow acoustic emissions to be detected; however, emissions of lower or higher frequencies may be detected.

The electrical signals which are generated by the transducer means 6 are electrically transferred to an amplifier means 8 of a suitable type as known in the art. Because the signals generated by the transducer means 6 are generally of relatively small magnitude, the amplifier means 8 is needed to increase the signals to levels sufficient for processing as subsequently described hereinbelow.

The amplified signal from the amplifier means 8 is applied to a filter and signal conditioner means 10 of a type known in the art. The filter portion of the means 10 operates so that only those ones of the corresponding electrical signals having frequencies within a predetermined second range of frequencies are provided for performing computations to determine the quantity of material separated or eroded from the conduit 2. In the preferred embodiment the filter is set or constructed to pass electrical signals having frequencies within the range from approximately 150 kilohertz to approximately 400 kilohertz.

The filtered signals are applied to the signal conditioner portion of the means 10 so that the filtered signals can be conditioned into a format suitable for use in a digital computer means such as a microprocessor means. For example, the signal conditioner portion of the means 10 can include an analog-to-digital converter means of a type known in the art.

The output from the filter and signal conditioner means 10 is transferred in the preferred embodiment to a microprocessor means 12 of a suitable type as known in the art. The microprocessor means 12 computes, in response to the filtered, conditioned electrical signals from the means 10, indications of the deterioration of the interior surface of the conduit 2. The microprocessor means 12 provides direct indications of the actual erosion in relation to the plastically deformed and/or fractured portions of the interior surface of the conduit 2 and the associated acoustic emission energy waves as represented by the electrical signals generated by the transducer means 6. It is important to note that the computation by the microprocessor means 12 is a direct relationship computation because the phenomena detected by the transducer means 6 are directly related to the amount of wear or deterioration of the interior surface of the conduit 2. Therefore, the present invention determines the deterioration of the conduit 2 based on the sensed acoustic emission energy released during the erosion process.

As discussed hereinabove the present invention can also determine the location or locations of the deterioration by detecting time differentials between electrical signals generated by multiple transducer means 6 disposed in spaced relation to each other along the conduit 2. In the preferred embodiment each of the multiple transducer means is associated with and functions with an amplifier means 8 and a filter and signal conditioning means 10 in the manner as described above.

Once the microprocessor means 12 has performed its computations, it provides suitable signals to a communication means for communicating the computed erosion and location thereof. The communication occurs in the preferred embodiment through a display means 14, such as a meter, which can be readily observed to note the instantaneous erosion and through a recorder means 16 for providing a tangible or hard-copy record of the monitored erosion. The display means 14 and the recorder means 16 are of suitable types as known in the art.

Figure 2:
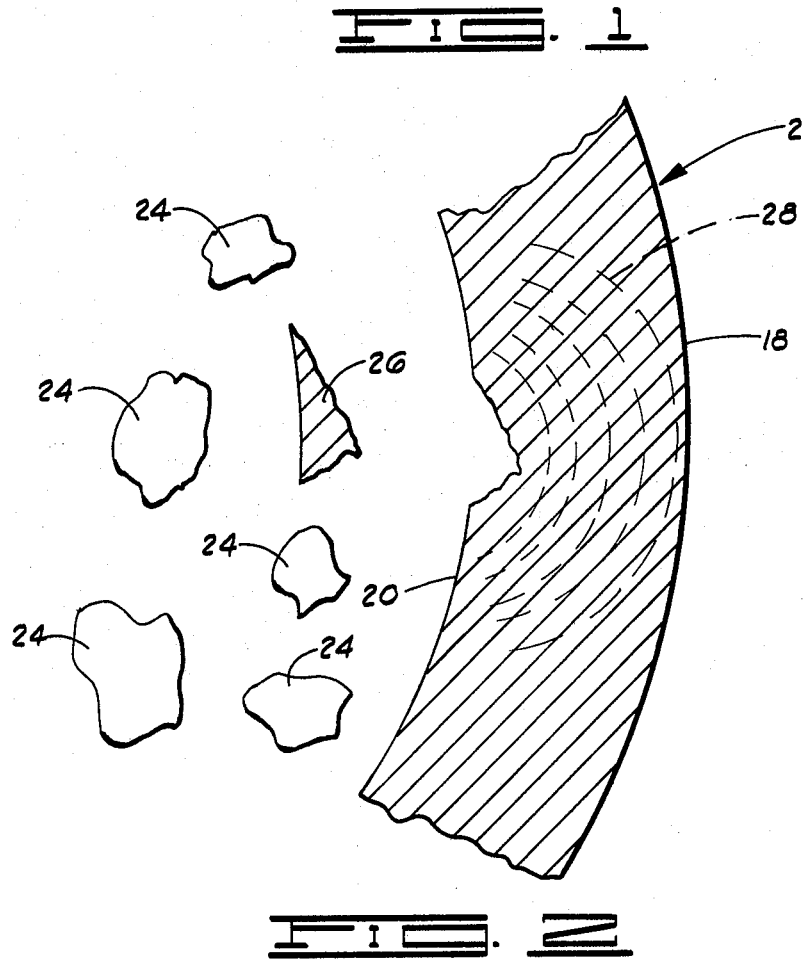
FIG. 2 is an enlarged schematic view of a portion of a conduit undergoing erosion due to particulate substances flowing therethrough.

With reference to FIG. 2 the preferred method and operation of the present invention will be more particularly described. FIG. 2 discloses an enlarged view of a portion of the conduit 2. This portion has an exterior or outer surface 18 and an interior or inner surface 20. Flowing through the conduit 2 in contact with the interior surface 20 is a stream comprising a fluid having particulate substances 24, such as sand, entrained therein.

As the particulate substances 24 travel along the conduit 2, they impinge upon the interior surface 20 of the conduit 2. These particulate substances 24 have different energies and, therefore, some impinge upon the interior surface 20 with energies which are insufficient to cause a plastic deformation or a fracture in the conduit 2. Other ones of the particulate substances 24 impinge with energies sufficiently great to create a change in the structure of the conduit 2. The pertinent changes with respect to the present invention are plastic deformations and fractures because these two changes cause acoustic emissions.

If the energy of the impinging particles 24 is too low to create a pertinent change (e.g., erosion damage) in the structure of the conduit 2, no acoustic emission energy is released; however, such relatively low energy particles may cause mechanical vibrations or "pinges" in the conduit 2 of the type disclosed to be detected by the device shown in U.S. Pat. No. 3,906,780 to Baldwin and the related documents identified above. Therefore, the detection of such vibrations or "pinges" may not indicate that erosion is occurring.

On the other hand, if the particles 24 have a relatively high energy, upon impingement these particles cause a plastic deformation or fracture which creates an acoustic emission of the type detected by the present invention. Because plastic deformations and fractures are in effect the erosion or deterioration of the conduit 2, the detection of the acoustic emissions directly indicates the amount of erosion or deterioration of the interior surface of the conduit resulting from the flowing stream.

The phenomenon of acoustic emission is a producer of stress waves in the conduit 2. Acoustic emission energy, or the energy of the produced stress waves, is produced by the motion of dislocations within the conduit 2 during plastic deformation. The motion of the dislocations produces high-frequency, low-energy stress waves that are detectable. Higher energy stress waves are also created by cracking in the conduit 2. It is these low-energy and high-energy stress waves, or acoustic emissions, which are detected by the present invention and which are directly related to the amount of deterioration or erosion of the interior surface 20 of the conduit 2.

With reference to FIG. 2, it will be assumed that one or more of the particles 24 has an energy sufficient to cause a local fracture in the conduit 2. As the sufficiently energized particles impinge upon the interior surface 20, they fracture one or more portions of the conduit 2. For example, as shown in FIG. 2 a portion 26 has been separated from the interior surface 20 of the conduit 2.

As the portion 26 is fractured and separated from the conduit 2, acoustic emission energy in the form of stress waves 28 is propagated through the conduit 2. This energy is detected by the transducer means 6 which is preferably attached to the outside or exterior surface 18 of the conduit 2. A preferable location includes an area at or near a portion of the conduit 2 where the flow direction of the flowing stream changes, such as at a bend in the conduit. The detected stress waves are converted into corresponding electrical signals which are electrically amplified, filtered, and conditioned prior to being input into the microprocessor means 12.

Upon receiving the input signals, the microprocessor means 12 analyzes them and provides indications of the instantaneous erosion occurring on the interior surface 20 of the conduit 2. If multiple transducer means are used, the microprocessor means 12 can also compute the location or locations of the erosion as described hereinabove. Time differentials can be determined from a clock associated with the microprocessor means.

In addition to detecting the erosion caused by particles impinging with a sufficient energy on the interior surface of the conduit 2 as described above with reference to FIG. 2, the present invention can also detect erosion caused by cavitation. During cavitation bubbles which are formed in the fluid flowing through the conduit 2 collapse against the interior surface of the conduit 2 and thereby erode the interior surface analogously to the impinging particles described hereinabove.

Although the conduit 2 has been illustrated in the drawings as a pipeline, the conduit 2 can be any suitable fluid-carrying element. For example, the conduit 2 may be a fluid passage through a valve, a pump, or a tubing found in a petroleum production system.

It is to be noted that the flow rate of the substance through the conduit 2 can also be optimized using the present invention. This optimizaton will maximize production rates without causing serious additional erosion damage to the equipment.

Thus, the present invention is well adapted to carry out the objects and attain the ends and advantages mentioned above as well as those inherent therein. While a preferred embodiment of the invention has been described for the purpose of this disclosure, numerous changes in the construction and arrangement of parts can be made by those skilled in the art which changes are encompassed within the spirit of this invention as defined by the appended claims.

What is claimed is:

1. A method for detecting the loss of conduit material from a conduit through which flows a fluid comprising:
   sensing the energy released when the conduit material is separated from the conduit as the fluid flows therethrough;
   determining the amount of material separated from the conduit based directly on the sensed released energy;
   wherein a particulate substance is entrained in the fluid and wherein the step of sensing the energy released includes:
   attaching to the conduit a transducer means responsive to a first range of frequencies of the released energy;
   converting, by means of said transducer means, the sensed released energy within the first range of frequencies into corresponding electrical signals;
   wherein the first range of frequencies of the released energy to which the transducer means is responsive includes the frequencies between approximately 100 kilohertz and approximately 500 kilohertz;
   wherein the step of sensing the energy released further includes electrically filtering the corresponding electrical signals so that only those ones of the corresponding electrical signals having frequencies within a second range of frequencies are provided for performing said step of computing the quantity of material separated from the conduit.

2. A method as defined in claim 1, wherein the second range of frequencies includes frequencies between approximately 150 kilohertz and approximately 400 kilohertz.

3. A method for detecting the loss of conduit material from a conduit through which flows a fluid comprising:
   sensing the energy released when the conduit material is separated from the conduit as the fluid flows therethrough;
   determining the amount of material separated from the conduit based directly on the sensed released energies;
   wherein a particulate substance is entrained in the fluid and wherein the step of sensing the energy released includes:
   attaching to the conduit a transducer means responsive to a first range of frequencies of the released energy;
   converting, by means of said transducer means, the sensed released energy within the first range of frequencies into corresponding electrical signals;
   wherein the step of sensing the energy released further includes electrically filtering the corresponding electrical signals so that only those ones of the corresponding electrical signals having frequencies within a second range of frequencies are provided for performing said step of computing the quantity of material separated from the conduit.

4. A method as defined in claim 3 wherein the second range of frequencies includes frequencies between approximately 150 kilohertz and approximately 400 kilohertz.

5. A method of detecting the loss of conduit material from a conduit through which flows a fluid effecting cavitation erosion of the conduit, comprising:
   sensing the energy released when the conduit material is separated from the conduit in response to the cavitation erosion effected by the fluid;
   computing the amount of material separated from the conduit based directly on the sensed release energy;
   wherein the step of sensing the energy released includes:
   attaching to the conduit a transducer means responsive to a first range of frequencies of the released energy;
   converting, by means of said transducer means, the sensed released energy within the first range of frequencies into corresponding electrical signals;
   wherein the first range of frequencies of the released energy to which the transducer means is responsive includes the frequencies beteen approximately 100 kilohertz and approximately 500 kilohertz;
   wherein the step of sensing the energy released further includes electrically filtering the corresponding electrical signals so that only those ones of the corresponding electrical signals having frequencies within a second range of frequencies are provided for performing said step of computing the quantity of material separated from the conduit.

6. A method as defined in claim 5, wherein the second range of frequencies includes frequencies between approximately 150 kilohertz and approximately 400 kilohertz.

7. A method of detecting the loss of conduit material from a conduit through which flows a fluid effecting cavitation erosion of a conduit, comprising:
sensing the energy released when the conduit material is separated from the conduit in response to the cavitation erosion effected by the fluids;
computing the amount of materials separated from the conduit based directly on the sensed released energy;
wherein the step of sensing the energy released includes:
attaching to the conduit a transducer means responsive to a first range of frequencies of the released energy;
converting, by means of said transducer means, the sensed released energy within the first range of frequencies into corresponding electrical signals;
wherein the step of sensing the energy released further includes electrically filtering the corresponding electrical signals so that only those ones of the corresponding electrical signals having frequencies within a second range of frequencies are provided for performing said step of computing the quantity of material separated from the conduit.

8. A method as defined in claim 7, wherein the second range of frequencies includes frequencies between approximately 150 kilohertz and approximately 400 kilohertz.

* * * * *